United States Patent
Numada et al.

(10) Patent No.: US 7,962,189 B2
(45) Date of Patent: Jun. 14, 2011

(54) NON-INVASIVE LIVING BODY MEASURING DEVICE

(75) Inventors: Shigehiro Numada, Kobe (JP); Toshiyuki Ozawa, Miki (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 11/485,564

(22) Filed: Jul. 12, 2006

(65) Prior Publication Data

US 2007/0015980 A1 Jan. 18, 2007

(30) Foreign Application Priority Data

Jul. 12, 2005 (JP) ................................ 2005-203727

(51) Int. Cl.
 *A61B 5/00* (2006.01)
 *A61B 6/00* (2006.01)
(52) U.S. Cl. ...................................... 600/322; 600/476
(58) Field of Classification Search .................. 600/318, 600/322, 476
See application file for complete search history.

(56) References Cited

U.S. PATENT DOCUMENTS

| | | | |
|---|---|---|---|
| 5,876,346 A | | 3/1999 | Corso |
| 6,120,461 A | * | 9/2000 | Smyth ........................... 600/558 |
| 7,155,043 B2 | * | 12/2006 | Daw ............................. 382/128 |
| 7,225,005 B2 | * | 5/2007 | Kaufman et al. ............. 600/322 |
| 2002/0058874 A1 | | 5/2002 | Ono et al. |
| 2002/0072658 A1 | | 6/2002 | Rice et al. |
| 2004/0162471 A1 | | 8/2004 | Ikeda et al. |

FOREIGN PATENT DOCUMENTS

| | | |
|---|---|---|
| EP | 0956812 A1 | 11/1999 |
| WO | WO 03/096903 A1 | 11/2003 |
| WO | WO 2006/065835 A2 | 6/2006 |

OTHER PUBLICATIONS

European Search Report for Application No. 06014381.5 dated Aug. 17, 2006.

* cited by examiner

*Primary Examiner* — Long V Le
*Assistant Examiner* — Michael T Rozanski
(74) *Attorney, Agent, or Firm* — Brinks Hofer Gilson & Lione

(57) ABSTRACT

A non-invasive living body measuring device is described, a representative one of which includes: a non-invasive living body measuring device for measuring the components contained in blood, comprising: an imaging part for imaging a living body; a display part; and a display control part for generating a blood vessel image showing blood vessels within a living body image obtained by the imaging part, and displaying the blood vessel image on the display part, wherein an index representing a suitable region for imaging by the imaging part is displayed on the display part.

10 Claims, 20 Drawing Sheets

NON-INVASIVE LIVING BODY MEASURING DEVICE

This application claims priority under 35 U.S.C. §119 to Japanese Patent Application No. JP2005-203727 filed Jul. 12, 2005, the entire content of which is hereby incorporated by reference.

FIELD OF THE INVENTION

The present invention relates to a non-invasive living body measuring device for measuring components contained in blood by analyzing blood vessels in a living body image obtained by imaging a living body.

BACKGROUND

There are known non-invasive living body measuring devices for measuring blood components by imaging a living body using an imaging means, and analyzing the blood vessels in the living body image (for example, refer to US2004/0162471A1). This non-invasive living body measuring device is provided with a light source, imaging part, and display part, and is mounted on the wrist of a user. This non-invasive living body measuring device illuminates a wrist containing blood vessels via a light source, and measures blood components from an image obtained by imaging the illuminated wrist, then displays the measurement result on the display part. In order to improve the accuracy of the blood component measurement, the device must positionally coincide with the measurement object blood vessel in the region to be imaged by the imaging part. The device disclosed in US2004/0162471A1 is positionally adjusted by the user while the user observes a living body image displayed on the display part of the non-invasive living body measuring device.

In the art disclosed in US2004/162471A1, the blood vessels in the living body image can not be displayed sharply, which makes it difficult for the user to determine whether or not the device is positioned in a suitable region for imaging a blood vessel.

SUMMARY

The scope of the present invention is defined solely by the appended claims, and is not affected to any degree by the statements within this summary.

In view of this information, the present invention provides a non-invasive living body measuring device that allows the user to easily determine whether or not the device is positioned in a region suitable for imaging a blood vessel.

The non-invasive living body measuring device of a first aspect of the present invention is a non-invasive living body measuring device for measuring the components contained in blood, comprising: an imaging part for imaging a living body; a display part; and a display control part for generating a blood vessel image showing blood vessels within a living body image obtained by the imaging part, and displaying the blood vessel image on the display part, wherein an index representing a suitable region for imaging by the imaging part is displayed on the display part.

The non-invasive living body measuring device of a second aspect of the present invention is a non-invasive living body measuring device for measuring the components contained in blood, comprising: an imaging part for imaging a living body; a display part; and a display control part generating a blood vessel image showing blood vessels within a living body image obtained by the imaging part, and displaying the blood vessel image on the display part, wherein an index representing a region suitable for imaging by the imaging part is provided on the display part.

The non-invasive living body measuring device of a third aspect of the present invention is a non-invasive living body measuring device for measuring the components contained in blood, comprising: an imaging part for imaging a living body; an analyzing part for specifying a blood vessel position in a living body image obtained by the imaging part by analyzing the living body image; and a determining part for determining whether or not a blood vessel is positioned within a suitable region for imaging by the imaging part.

The non-invasive living body measuring device of a fourth aspect of the present invention is a non-invasive living body measuring device for measuring the components contained in blood, comprising: a device body including an imaging part for imaging a living body, and an analyzing part for analyzing blood vessels in a captured living body image; a movable loading part to which the device body is detachably mounted; and a mounting part for holding the loading pert, and that can be mounted on a living body, wherein the loading part includes a first index representing a suitable region for imaging by the imaging part.

DETAILED DESCRIPTION OF THE PREFERRED EMBODIMENTS

First Embodiment

Figure 1:
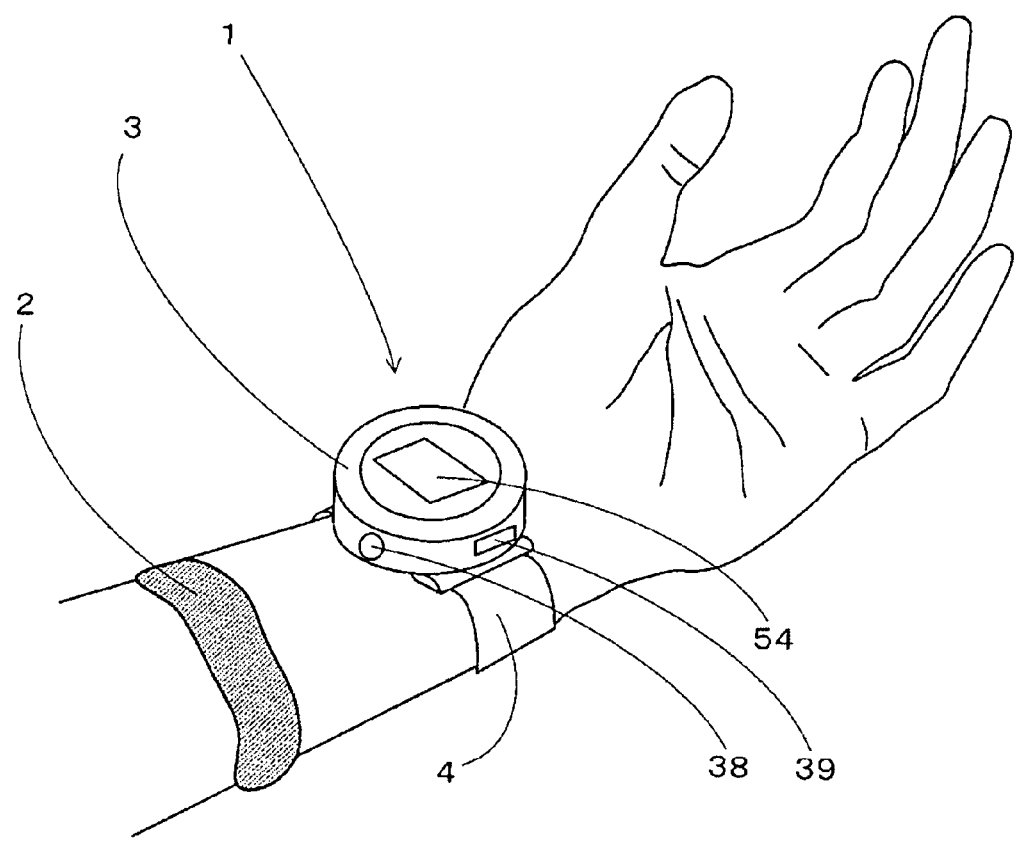
FIG. 1 briefly shows the structure of a non-invasive living body measuring device 1 of a first embodiment of the present invention.

FIG. 1 briefly shows the structure of a non-invasive living body measuring device 1 of a first embodiment of the present invention. As shown in FIG. 1, the non-invasive living body measuring device 1 is a wristwatch-type blood component analyzer that is provided with a device body 3 and holder 4. The body 3 is installed on the wrist of a person via the holder 4. The body 3 is mounted so as to be positionally adjustable in the circumferential direction of the wrist via the holder 4. A power/execute key 38 and menu key 39 are provided on the side of the body 38 to allow the user to operate the non-invasive living body measuring device 1. A pressure band 2 (cuff) is mounted on the arm of the user nearer the heart than the wrist. The pressure band 2 impairs the blood flow to the wrist area so as to expand the blood vessels (veins) of the wrist by applying a predetermined pressure to the wrist of the user. When measurement is performed with the pressure band 2 applying pressure to the wrist, the blood vessels can be easily imaged, thus improving the accuracy of the blood analysis.

Figure 2:
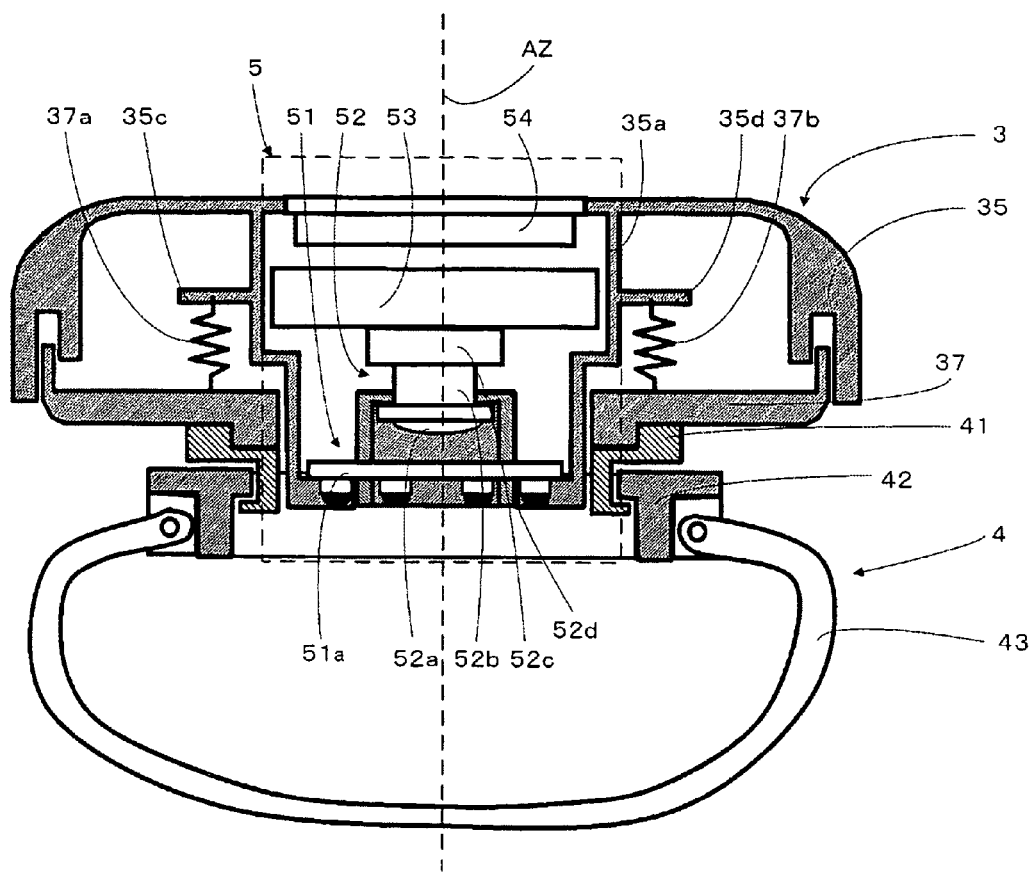
FIG. 2 is a cross section view showing the structure of the non-invasive living body measuring device 1.

FIG. 2 is a cross section view showing the structure of the non-invasive living body measuring device 1. As shown in FIG. 2, the body 3 is provided with an external case 35, a back cover 37 disposed on the back side of the external case 35, and a connecting member 41 mounted to the bottom of the back cover 37. A cylindrical unit holder 35a is formed in the center of the external case 35 to accommodate a measuring unit 5, which is described later. A hollow space for accepting the unit holder 35a is formed in the center of the back cover 37 and connecting member 41. A pair of projections 35a and 35d extend horizontally from the intermediate part of the outer wall of the unit holder 35a. The projection 35 and back cover 37, and the projection 35d and back cover 37 are respectively connected via compression springs 37a and 37b. The external case 35 is forced toward the back cover 37 via these compression springs 37a and 37b. A depressed concavity shaped connecting part is formed on the side surface of the connecting member 41, and is connectable to the connecting part of a support platform 42, which is described later.

The holder 4 is configured by a support platform 42 and wrist band 43. The top surface of the support platform 42 is rectangular, and a circular opening is formed in the center to engage the connecting member 41 of the body 3. A connecting part is formed at the edge of the opening so as to rotatably connect to the connecting member 41 around the axis AZ. An elastic rubber wristband 43 is mounted to the support platform 42. The exterior case 35 and back cover 37 are made of material that does not transmit light.

A measuring unit 5 is supported by the unit holder 35a. The measuring unit 5 is configured by a light source 51, imaging part 52, control part 53, and display part 54; the light source 51, imaging part 52, control part 53 are connected via wiring, flat cable (not shown) or the like so as to be mutually capable of handling electrical signals.

Figure 3:
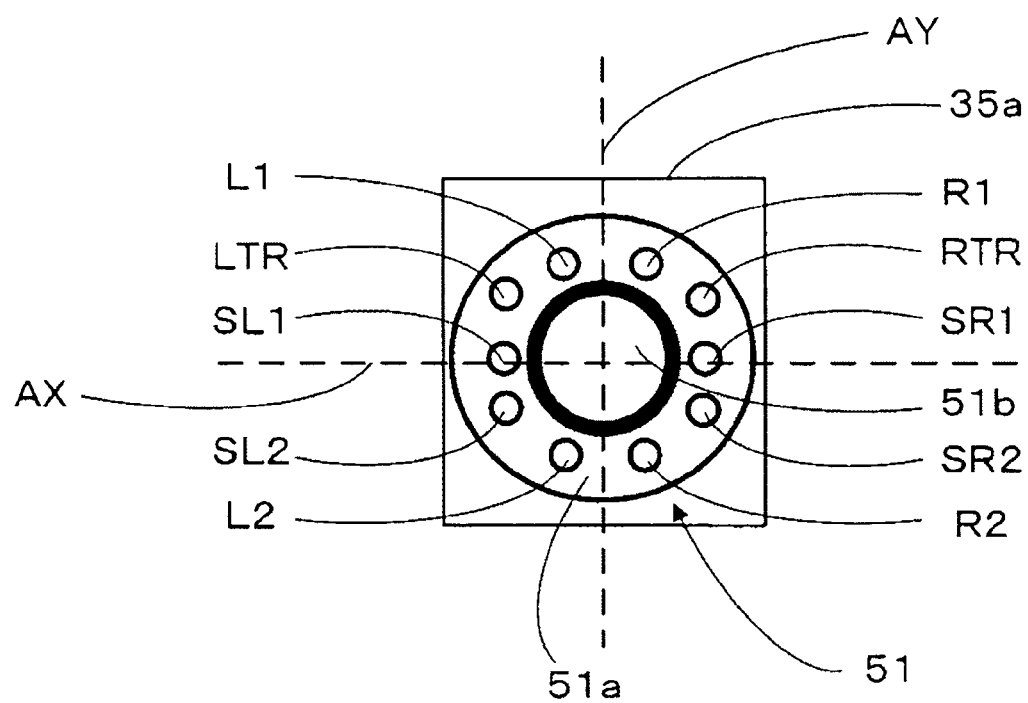
FIG. 3 is a plan view showing the structure of a light source 51.

The light source 51 is described below. FIG. 3 is a plan view showing the structure of a light source 51. As shown in FIG. 3, the light source 51 is configured by a circular disk like holding plate 51a, and eight light-emitting diodes R1, R2, SR1, SR2, L1, L2, SL1, SL2 and two phototransistors RTR and LTR, which are held on the holding plate 51a. A circular opening 51b is formed in the center of the holding plate 51a to allow the passage of light rays to the imaging part 52.

Figure 4:
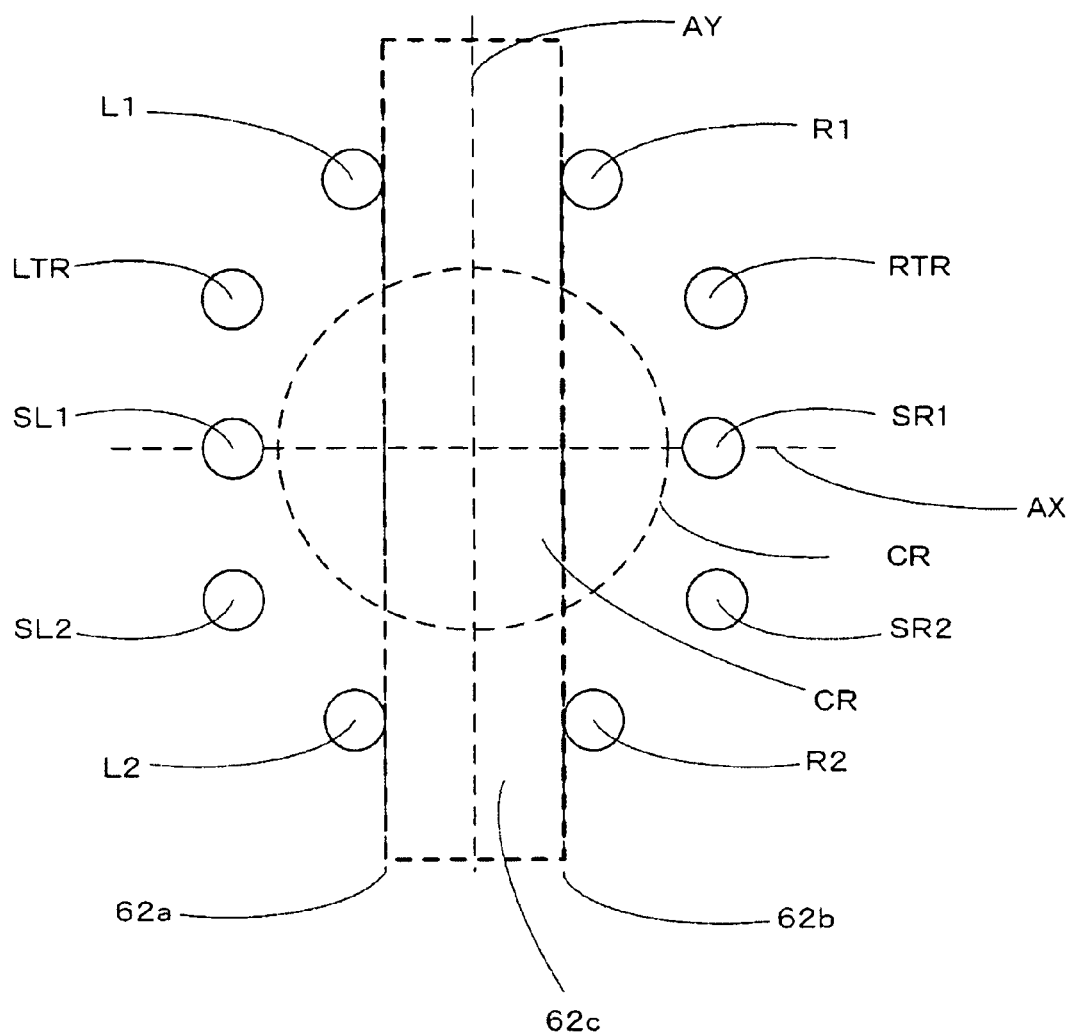
FIG. 4 shows the positional relationship of the phototransistor and light-emitting diode provided on a holding plate 51*a*.

FIG. 4 shows the positional relationship of the phototransistor and light-emitting diode provided on the holding plate 51a. As shown in FIG. 4, the light-emitting diodes R1, R2, L1, and L2 are symmetrically arranged on the first axis AY and second axis AX, which are perpendicular and mutually intersect while passing through the center of the opening 51b; the light-emitting diodes SR1, SR2, SL1, and SL2, and the phototransistors RTR and LTR are arranged symmetrically on the first axis AY. When the non-invasive living body measuring device 1 is mounted on the wrist, the imaging region CR on the wrist surface is imaged by the imaging part 52, and the region is displayed on the display part 54. A region 62c, which is disposed between an index line 62a on the light-emitting diodes L1 and L2 side, and an index line 62b on the light-emitting diodes R1 and R2 side, is a region suitable for imaging via the imaging part 52, that is, a region that positions the blood vessel for imaging. The index lines 62a and 62b are displayed on the display part 54 via the control part 53. When blood components are analyzed, the position of the body 3 is adjusted so as to position an optional blood vessel in the wrist within the region 62c. The blood vessel is then illuminated by infrared light (mid point wavelength=805 nm) from both sides via the light-emitting diodes R1, R2, L1, and L2. The light-emitting diodes SR1 and SR2 illuminate the region that does not include the blood vessel, and the light reflected from this region is received by the phototransistor RTR. Similarly, the light-emitting diodes SL1 and SL2 illuminate the region that does not include the blood vessel, and the light reflected from this region is received by the phototransistor LTR. The control part 53 calculates an index M representing the amount of blood in the tissue excluding the blood vessel based on the amount of light received by the phototransistors RTR and LTR. The index M is used to correct the measured blood component (hemoglobin concentration D, in the present embodiment) value.

The structure of the imaging part 52 is described below. As shown in FIG. 2, the imaging part 52 is configured by a lens 52a for focusing reflected light, a lens barrel 52b that fixedly holds the lens 52a, and a CCD camera 52c for capturing an image; the imaging part 52 captures the image of the imaging region CR. The lens 52a and lens barrel 52b are inserted in a cylindrical light shield tube 52d with a black interior. The CCD camera 52c captures the formed image and sends it to the control part 53 as image signals.

Figure 5:
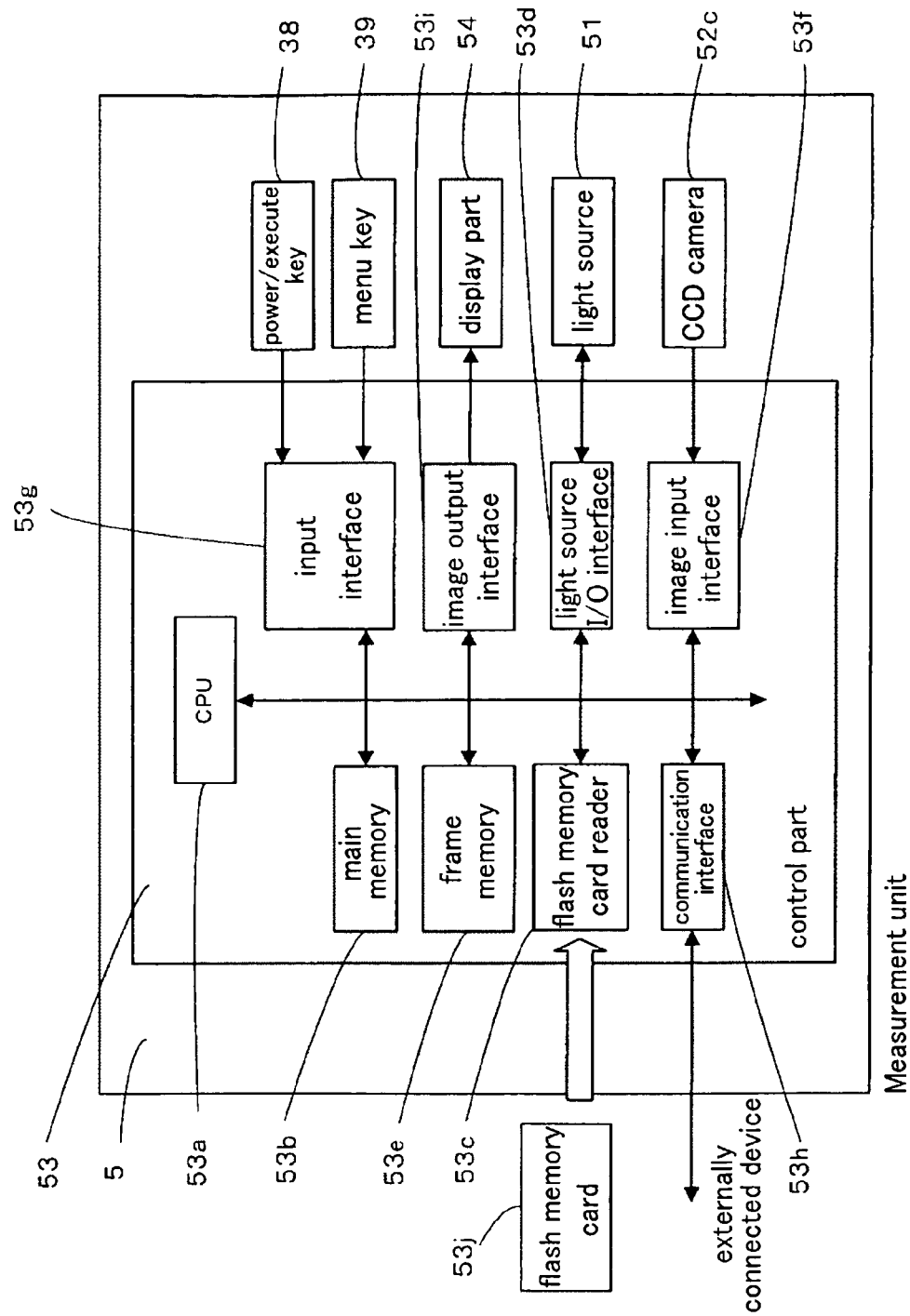
FIG. 5 is a block diagram showing the structure of a measuring unit 5.

The structure of the control part 53 is described below. The control part 53 is provided at the top of the CCD camera 52c. FIG. 5 is a block diagram showing the structure of a measuring unit 5. As shown in FIG. 5, the control part 53 is provided with a CPU 53a, main memory 53b, flash memory card reader 53c, light source I/O interface 53d, frame memory 53e, image input interface 53f, input interface 53g, communication interface 63h, and image output interface 53i. The control part 53 is provided with a CPU 53a, main memory 53b, flash memory card reader 53c, light source I/O interface 53d, frame memory 53e, image input interface 53f, input interface 53g, communication interface 63h, and image output interface 53i are connected via a data transfer cable so as to be capable of mutual data transmissions.

Thus, the CPU 53a reads and writes data from/to the main memory 53b, flash memory card reader 53c, and frame memory 53e, and sends and receives data to/from the light source I/O interface 53d, image input interface 53f, input interface 53g, image output interface 53i, and communication interface 53h.

The CPU 53a executes computer programs loaded in a ROM not shown in the drawing, and main memory 53b. The device functions as a non-invasive living body measuring device when a computer program, described later, is executed by the CPU 53a.

The main memory 53b is configured by an SRAM, DRAM or the like. The main memory 53b is used when reading the computer programs stored in a flash memory card 53j or ROM not shown in the drawing. The main memory 53b is used as the work area of the CPU 53a when the computer programs are executed.

The flash memory card reader 53c is used to read data stored on the flash memory card 53j. The flash memory card 53j has a flash memory (not shown in the drawing), and holds data even when not supplied power from an external source. Computer programs executed by the CPU 53a, and data used by these programs are stored on the flash memory card 53j.

For example, an operating system conforming to TRON specifications is installed on the flash memory card 53j. The operating system is not limited to this operation system inasmuch as the operating system provides a graphical user interface environment, such as Microsoft Windows (registered trademarks) manufactured by Microsoft corporation. In the present description, the computer program of the present embodiment operates in the environment provided by such an operating system.

The light source I/O interface 53d is an analog interface with D/A converter and A/D converter. The light source I/O interface 53d is electrically connected via an electrical signal line to the eight light-emitting diodes R1, R2, SR1, SR2, L1, L2, SL1, and SL2, and two phototransistors RTR and LTR provided in the light source 51. The light source I/O interface 53d receives detection signals from the phototransistors RTR and LTR, and transmits control signals to the light-emitting diodes R1, R2, SR1, SR2, L1, L2, SL1, and SL2. The light source I/O interface 53d controls the current supplied to the light-emitting diodes R1, R2, SR1, SR2, L1, L2, SL1, and SL2 based on a computer program described later.

The frame memory 53e is an SRAM, DRAM or the like. The frame memory 53e is used to accommodate data when the image input interface 53f, which is described later, executes image processes.

The image input interface 53f is provided with a video digitizing circuit (not shown in the drawing) that includes an A/D converter. The image input interface 53f is electrically connected to the CCD camera 52c, and receives image signals from the CCD camera 52c. The image signals received from the CCD camera 52c are subjected to A/D conversion by the image input interface 53f. The digitally converted image signals are stored in the frame memory 53e.

The input interface 53g is an analog interface with an A/D converter. The power/execute key 38 and menu key 39 are electrically connected to the input interface 53g. Thus, the user selects an operation item of the device via the menu key 39, and turns ON/OFF the power source of the device and executes the selected operation of the device via the power/execute key 38.

The communication interface 53h is a serial interface, such as, for example, a USB, IEEE1394, RS232C or the like, or a parallel interface such as a SCSI or the like. The control part 53 uses a predetermined communication protocol to send and receive data to/from an externally connected device, such as a mobile computer, potable telephone or the like via the communication interface 53h. Thus, the control part 53 sends measurement result data to an externally connected device via the communication interface 53h.

The image output interface 53i is electrically connected to the display part 54, and outputs image signals to the display part 54 based on the image data from the CPU 53a.

The display part 54 is described below. As shown in FIG. 2, the display part 54 is provided on the top of the measuring unit 5, and is supported by the external case 35. The display part 54 is a liquid crystal display, that displays images according to the image signals received from the image output interface 53i. The image display is switchable according to the status of the non-invasive living body measuring device 1, for example, a screen corresponding to the standby state, the measurement end condition or the positioning the blood vessel is displayed on the display part 54.

Figure 6:
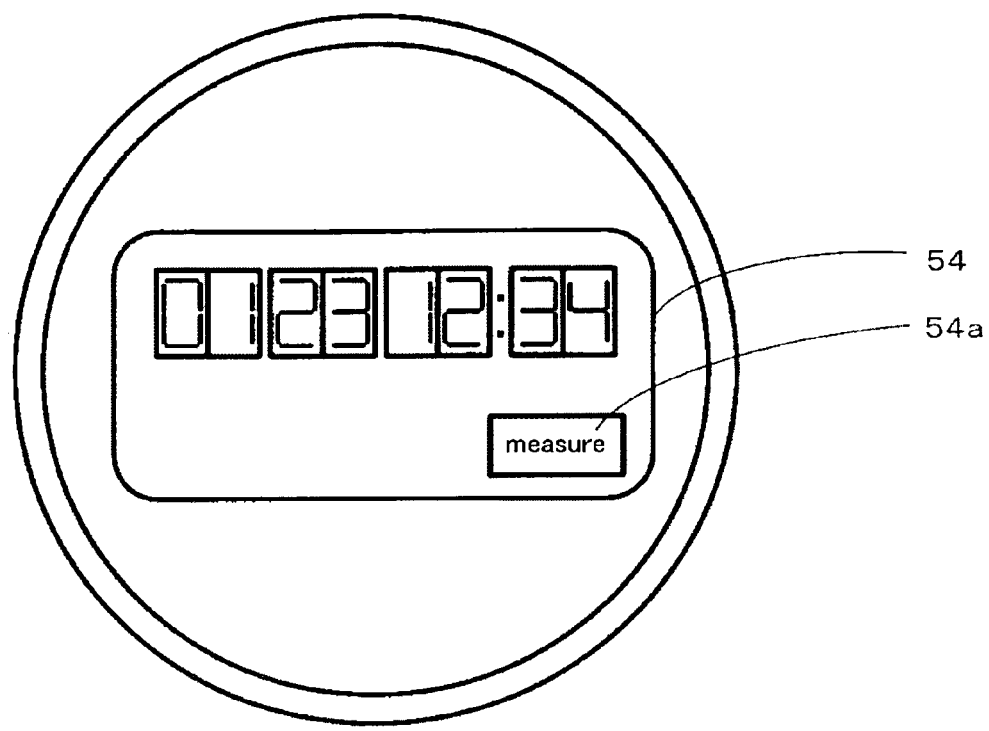
FIG. 6 shows an example of screen when the non-invasive living body measuring device 1 is in the standby mode.

FIG. 6 shows an example of screen when the non-invasive living body measuring device 1 is in the standby mode. As shown in FIG. 6, when the non-invasive living body measuring device 1 is in the standby state, the date and time are displayed in the center of the screen of the display part 54. At the bottom right of the screen of the display part 54 is a menu display region 54a, the operation of the non-invasive living body device 1 is displayed when the power/execute key 38 is pressed, and "measurement" is displayed in the standby state.

Figure 7:
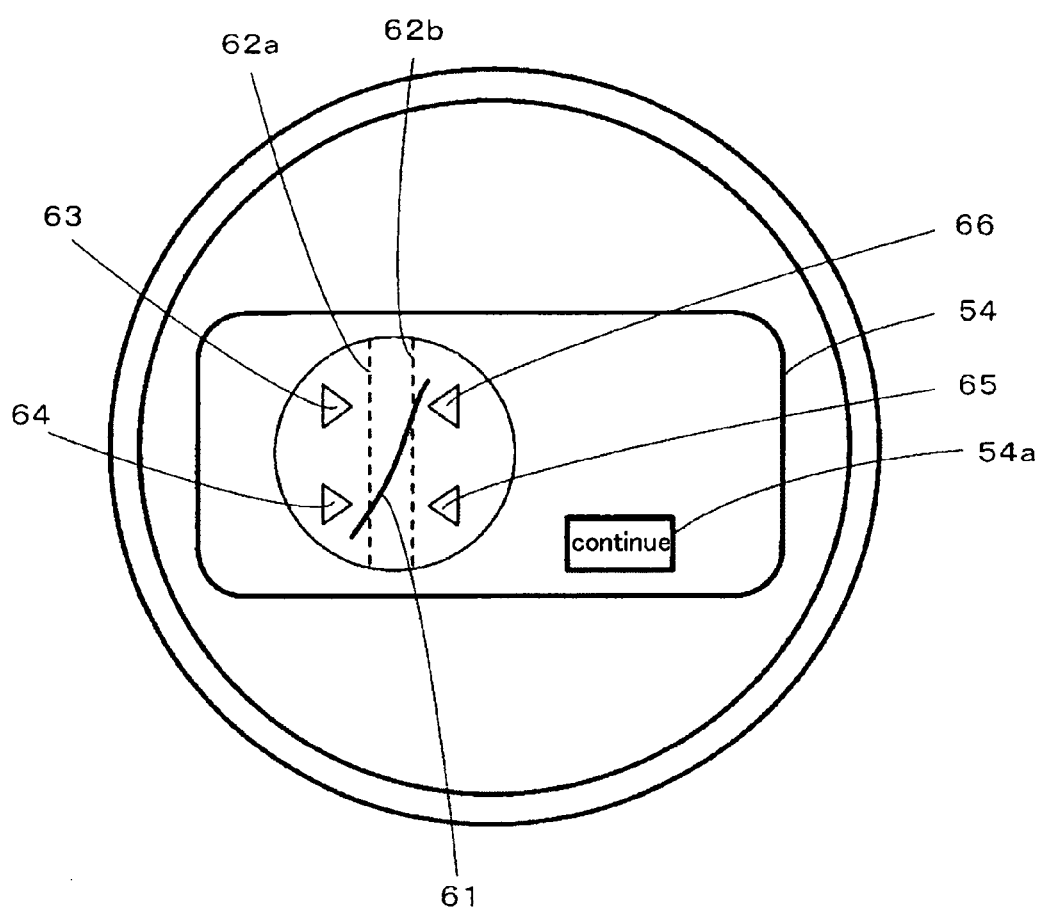
FIG. 7 shows an example of a screen when the non-invasive living body measuring device 1 is aligned in position with a blood vessel.

FIG. 7 shows an example of a screen when the non-invasive living body measuring device 1 is aligned in position with a blood vessel. As shown in FIG. 7, when the non-invasive living body measuring device 1 is positioned on a blood vessel, a captured image, and blood vessel pattern 61 and index lines 62a and 62b indicated in red color are displayed. Furthermore, direction markers 63, 64, 65, and 66 are displayed around the index lines 62a and 62b. Each marker is capable of being lighted, such that when the blood vessel pattern 61 is not positioned so as to be accommodated within a region 62c between the index lines 62a and 62b, the control part 53 causes each marker to light, so as to indicate to the user the direction in which to move the device body 3 to have the blood vessel pattern 61 positioned within the region 62c.

The movement of the device body 3 indicated by the lighted markers is briefly described below. In FIG. 7, when the marker 63 and marker 64 are lighted, the user must move the device body 3 to the right in FIG. 7, and when the marker 65 and marker 66 are lighted, the user must move the device body 3 to the left in FIG. 7. When marker 63 and marker 65 are lighted, the user must rotate the device body 3 clockwise, and when the marker 64 and marker 66 lighted, the user must rotate the device body 3 counterclockwise. When, for example, the device 3 is positioned with the blood pattern 61 as shown in FIG. 7, the control part 53 causes the marker 63 and marker 65 to light, and the user rotates the device body 3 clockwise. According to this configuration, when the imaging part 52 is positionally adjusted in a region suited for imaging a blood vessel, the positionally adjusting the imaging part 52 is simple since the user can easily comprehend the direction in which to move the device body 3.

The index line 62a and index line 62b are displayed in red when the blood vessel pattern 61 is not positioned within the region 62c (FIG. 4), and the index line 62a and index line 62b are displayed in blue when the blood vessel pattern 61 is within the region 62c. Thus, the user can easily comprehend whether or not the blood vessel pattern 61 is positioned within the region 62c.

When the blood vessel is being positioned, "continue" is displayed in the menu display region 54a, and when the blood vessel pattern 61 has been positioned within the region 62c, the index lines 62a and 62b are displayed in blue, the power/execute key 38 become valid, and the user presses this key to continue measurement.

Figure 8:
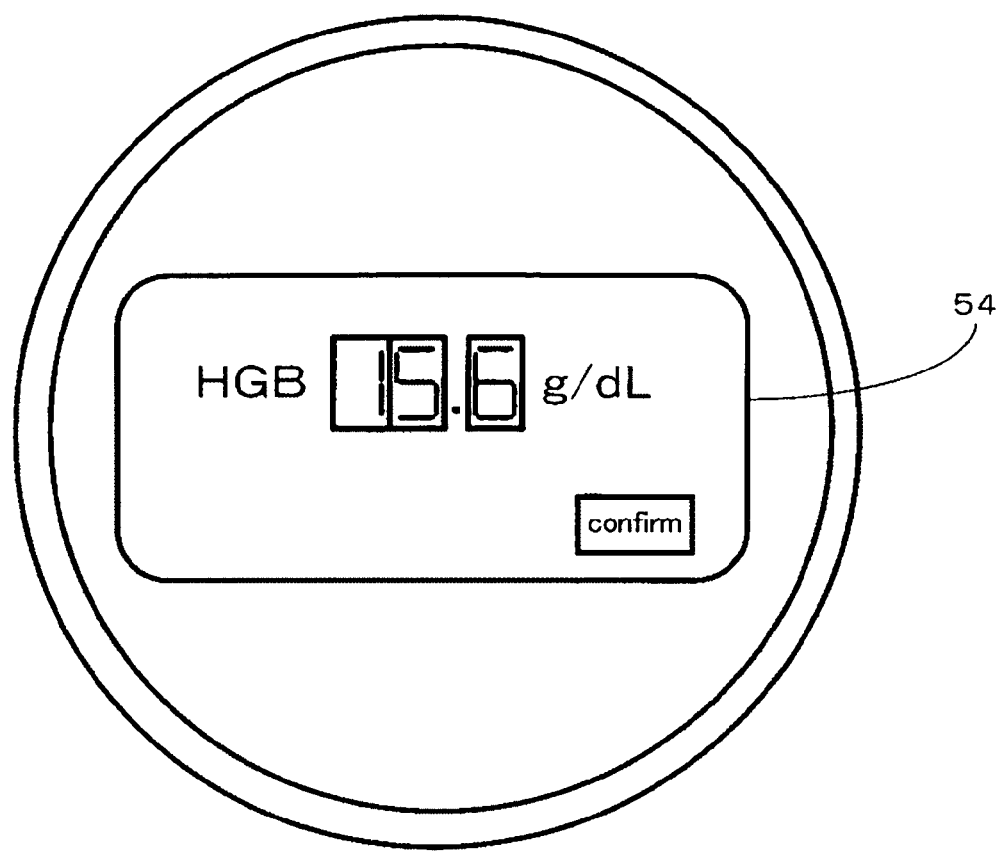
FIG. 8 shows an example of a screen when the non-invasive living body measuring device 1 has completed a measurement.

FIG. 8 shows an example of a screen when the non-invasive living body measuring device 1 has completed a measurement. As shown in FIG. 8, when the blood component, hemoglobin, concentration measurement result is "15.6 g/dl," the information is displayed on the display part 54 in a digital display that is easy for the user to see. At this time, "confirm" is displayed in the menu display region 54a.

The measurement operation performed by the non-invasive living body measuring device 1 is described below. First, as shown in FIG. 1, the non-invasive living body measuring device 1 is mounted on the wrist, and the pressure band 2 is attached to the arm of the user. At this time, the arm of the user is subjected to a predetermined pressure via the pressure band 2, such that the blood flow is impaired in the wrist region causing the blood vessels in the wrist to swell. Next, the user presses the power/execute key 38 provided on the non-invasive living body measuring device 1 to turn ON the power source of the non-invasive living body measuring device 1, whereupon the device enters the standby state and the standby condition screen shown in FIG. 6 is displayed on the display part 54.

Figure 9:
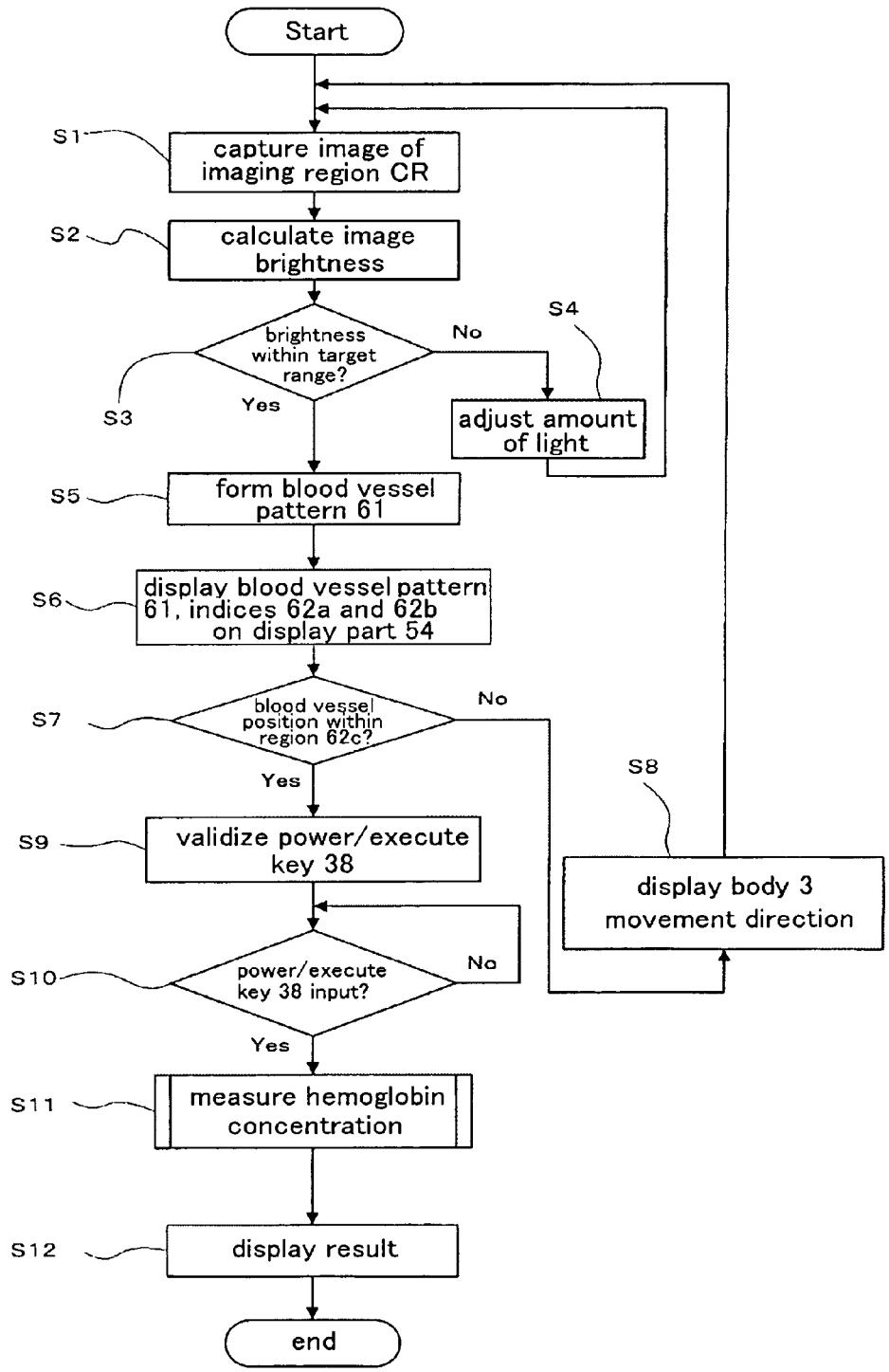
FIG. 9 is a flow chart showing the measurement operation performed by the non-invasive living body measuring device 1.

FIG. 9 is a flow chart showing the measurement operation performed by the non-invasive living body measuring device 1. When the standby condition screen is displayed on the display part 54 and the user presses the power/execute key 38, the screen shown in FIG. 7 appears on the display part 54. At this time, the CPU 53a lights the light-emitting diodes R1, R2, L1, and L2 provided in the light source 51 a predetermined amount, illuminates the imaging region CR (FIG. 4), and captures an image of the illuminated imaging region CR (step S1).

Figure 10:
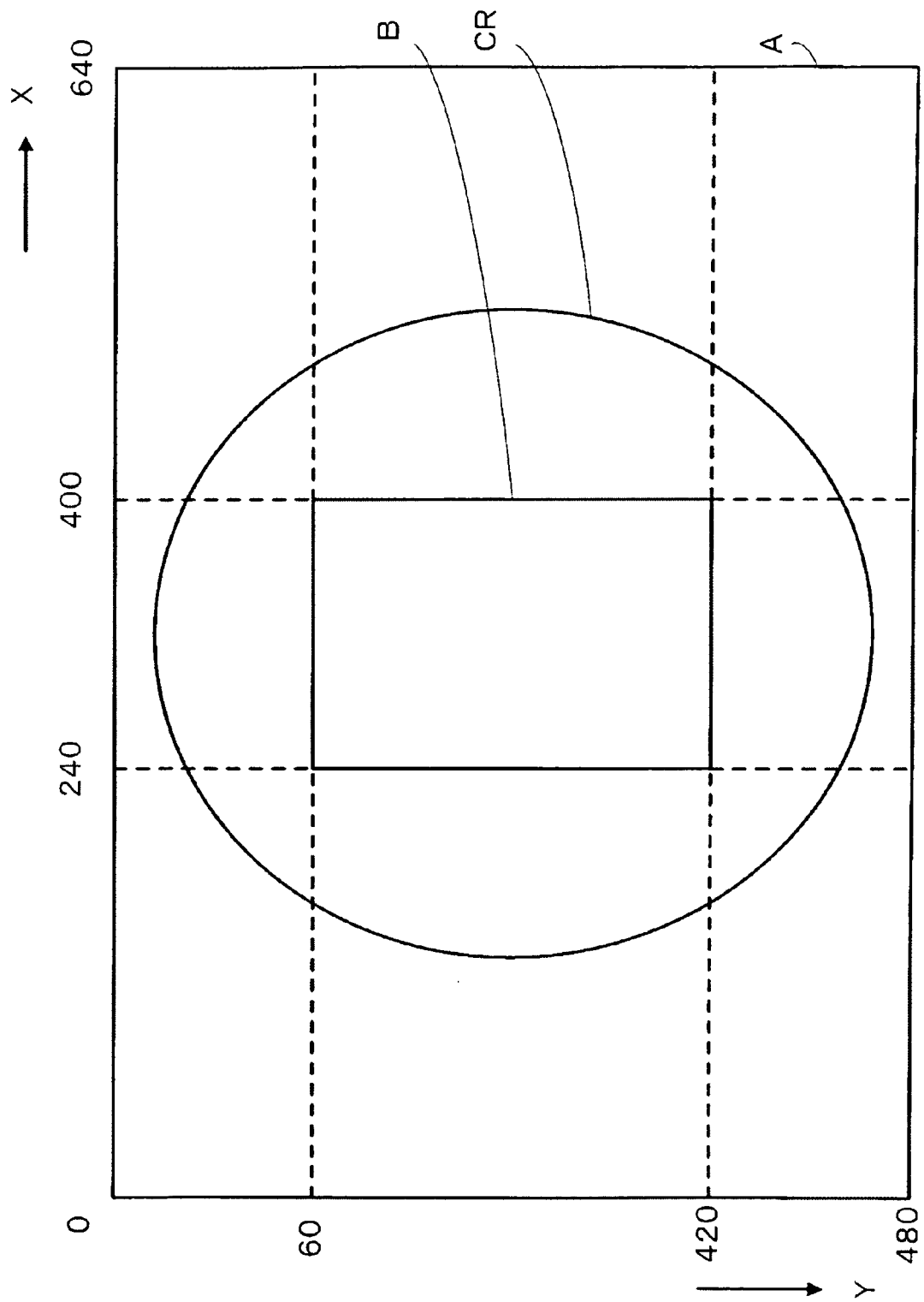
FIG. 10 is a coordinate division diagram of two-dimensional coordinates x and y within a range where a rectangular region including an imaging region CR is $0 \leq y \leq 480 \leq$, $0 \leq x \leq 640$.

FIG. 10 is a coordinate division diagram of two-dimensional coordinates x and y within a range where a rectangular region including an imaging region CR is $0 \leq y \leq 480$, $0 \leq x \leq 640$. As shown in FIG. 10, the CPU 53a divides the two-dimensional coordinates x and y of region A setting the left uppermost pixel coordinates of a rectangular region A that includes an image of the imaging region CR as (0, 0), selects four points (240, 60), (400, 60), (240, 420), and (400, 420) from the center point of the divided coordinates, and determines the average brightness of a region B circumscribed by these four points (step S2). The points of region B determined for determining average brightness are not limited to the above arrangement inasmuch as other points may be used.

Figure 11:
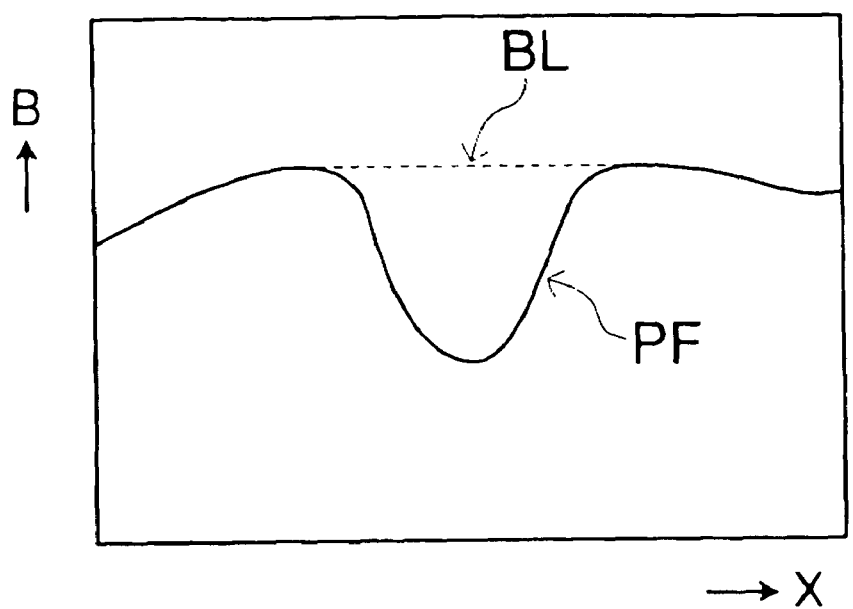
FIG. 11 shows an example of a brightness profile (brightness profile PF) of pixels in the x direction at a specific y coordinate.
Figure 12:
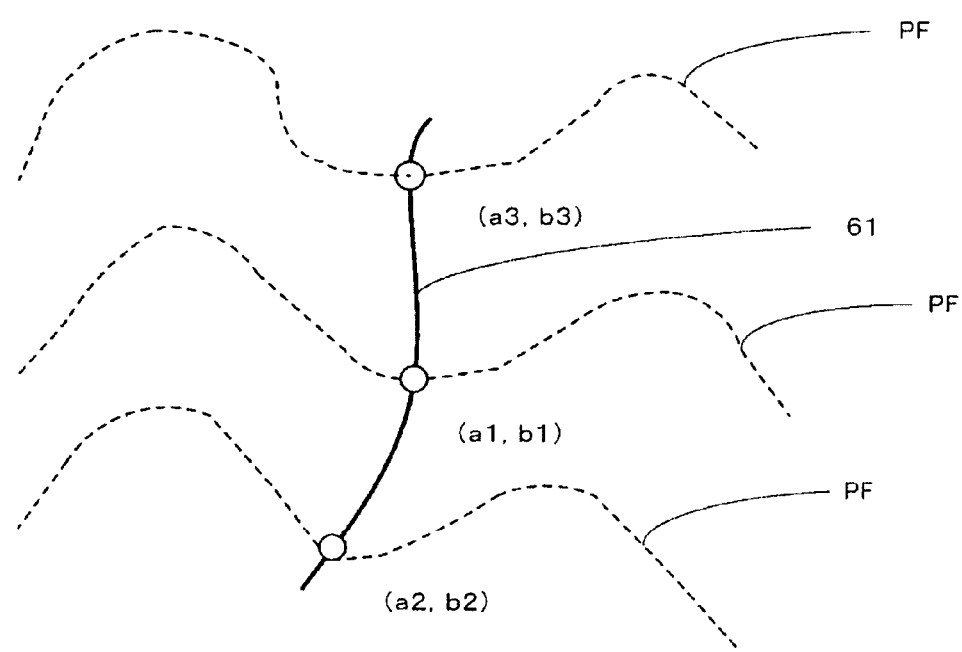
FIG. 12 illustrates the method for determining the position of a blood vessel.

Region B may also be polygonal or circular rather than rectangular. Next, the CPU 53a determines whether or not the brightness of the region B is within a target range. When the brightness of the region B is outside the target range, the amount of currents flowing to the light-emitting diodes R1, R2, L1, and L2 are adjusted using the light source I/O interface 53d to adjust the amount of light (step S4), and the process returns to step S1. When the brightness of the region B is within the target range (step S3: YES), the CPU 53a determines the brightness of the pixels from end to end of the x coordinates at which the value of the y coordinate of the allocated region A is 40. Thus, as shown in FIG. 11, a brightness profile (brightness profile PF) is determined for the pixels in the x direction at a specific y coordinate. Then, the CPU 53a shifts twenty pixels in the y axis direction, and determines the brightness from end to end of the x coordinates at which the y coordinate value is 60. The CPU 53a repeats the operation until the value of the y coordinate becomes 440, and determines a brightness profile at each y coordinate value. The CPU 53a extracts the point of lowest brightness (hereinafter referred to as "lowest brightness point") from among the extracted brightness profile, and stores the point data in the frame memory 53e. FIG. 12 illustrates the method for determining the position of a blood vessel. That is, as shown in FIG. 12, the CPU 53a sets the lowest brightness point at (a1, b1) near the center of the image of the imaging region CR, and connects the adjacent lowest brightness points (a2, b2) and (a3, b3) in the vertical direction with the lowest brightness point (a1, b1). Next, the CPU 53a connects the points adjacent in the vertical direction with the lowest brightness point (a2, b2), and connects the points adjacent in the vertical direction with the lowest brightness point (a3, b3). The CPU 53a repeats the operation for the entire region of the image, extracts the blood vessel as a line segment, and creates a blood vessel pattern 61 (step S5). As shown in FIG. 7, the CPU 53a displays the image of the captured imaging region CR on the display part 54, then displays the blood vessel pattern 61 created in step S5, the index lines 62a and 62b (FIG. 4) stored in the flash memory card 53j, and the markers 63, 64, 65, and 66 (step S6). Then, the CPU 53a determines whether or not the blood vessel pattern 61 is positioned in the region 62c (FIG. 4) (step S7). When the blood vessel pattern 61 is not positioned within the region 62c (step S7: NO), the CPU 53a lights the markers 63, 64, 65, and 66, to indicates the direction in which the user should move the device body 3 (step S8), and the process returns to step S1.

When the blood vessel pattern 61 is within the region 62c (step S7: YES), the CPU 53a validates the power/execute key 38 making it is possible for measurement to continue. At this time, the CPU 53a alerts the user to the validation of the power/execute key 38 via a chirping sound (step S9). Then, the CPU 53a awaits input from the power/execute key 38 (step S10). When the user presses the power/execute key 38 and measurement is supported (step S10: YES), the CPU 53a measures the concentration of hemoglobin (step S11), and displays the measurement result on the display part 54 (step S12).

Figure 13:
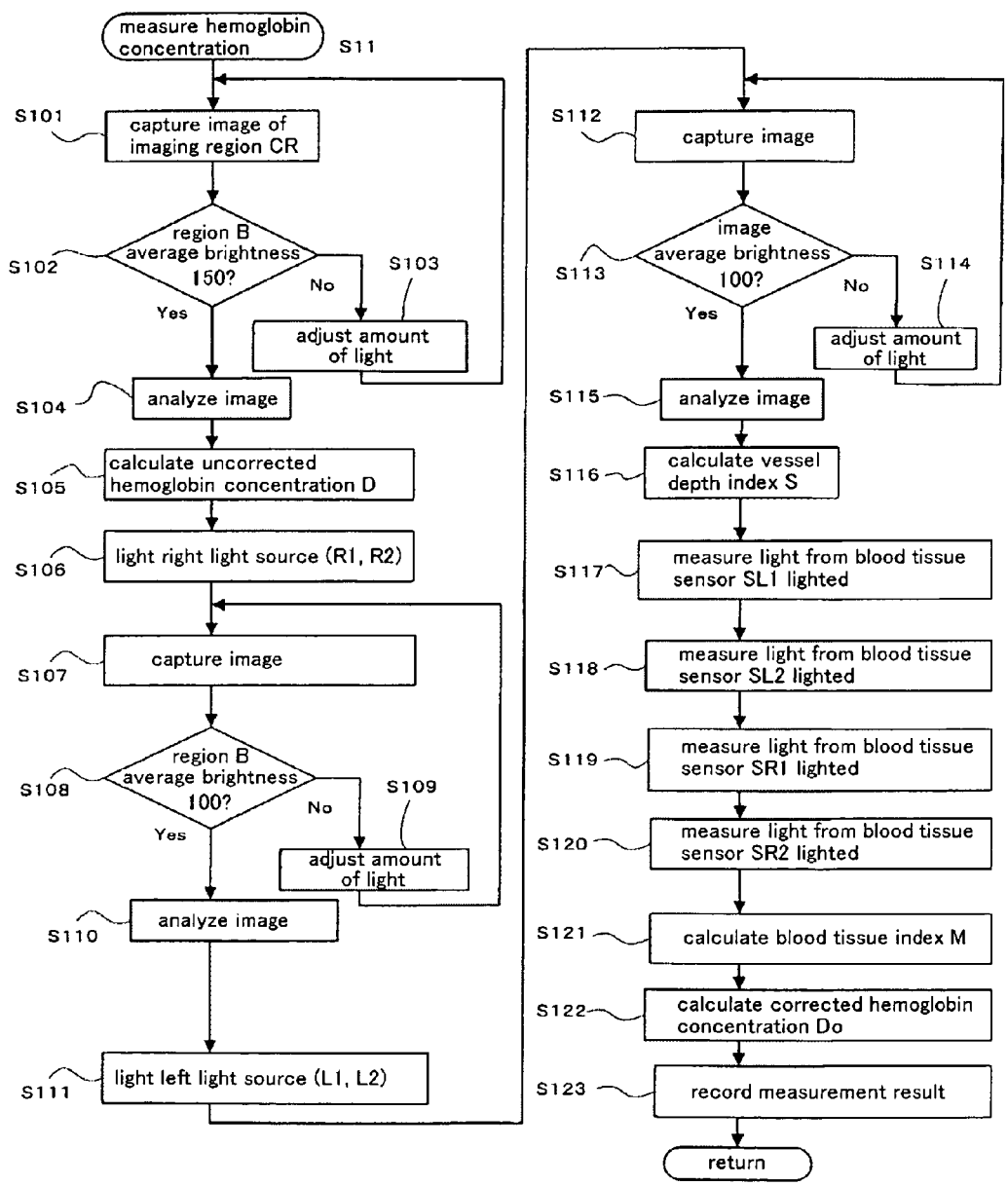
FIG. 13 is a flow chart showing details of the hemoglobin concentration measurement process executed in step S11 of the flow chart shown in FIG. 9.

FIG. 13 is a flow chart showing details of the hemoglobin concentration measurement process executed in step S11 of the flow chart shown in FIG. 9. As shown in FIG. 13, the CPU 53a controls the light source I/O interface 53d, the light-emitting diodes R1, R1, L1, and L2 illuminate the imaging region CR (FIG. 4), and the image is captured by the imaging part 52 (step S101). Then, the CPU 53a determines the average brightness of the region B shown in FIG. 10 similar to the process of step S3, and determines whether or not the average brightness of region B exceeds 150 (step S102). When the average brightness exceeds 150, the amount of current flowing to the light-emitting diodes R1, R2, L1, and L2 is adjusted using the light source I/O interface 53d to adjust the amount of light (step S103), and the process returns to step S101.

The brightness value in the present embodiment is a digitally converted value (variable 0~255) of an 8-bit A/D converter with an image input interface 53f. Since the magnitude of the image signal input from the CCD camera 52c is proportional to the image brightness, the image signal A/D conversion value (0~255) is set as the brightness value.

Figure 14:
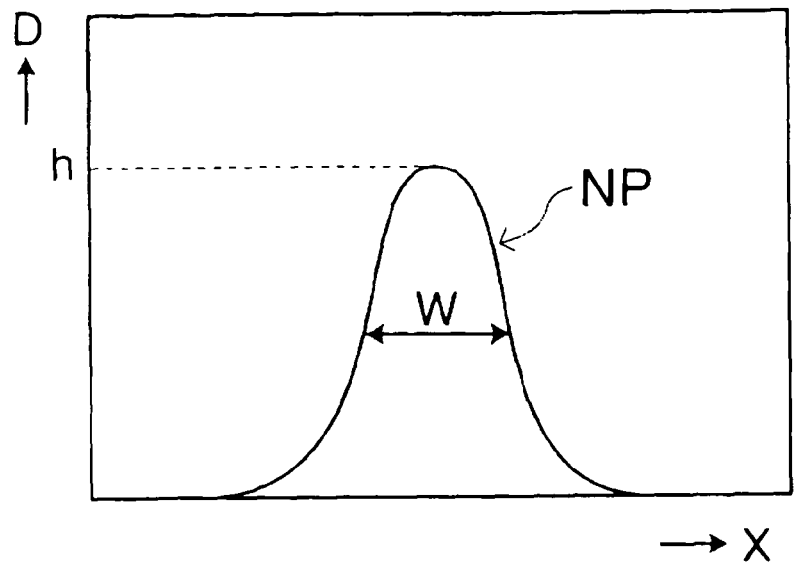
FIG. 14 shows a distribution of density D relative to position X.

When the average brightness value of the region B is over 150 (step S102: YES), the CPU 53a creates a brightness profile (distribution of brightness B relative to position X) PF (FIG. 11) relative to the AX axis in the imaging region CR (FIG. 4), and reduces the noise component using a Fast Fourier Transformation or the like. Then, the CPU 53a standardizes the brightness profile PF by a baseline BL. The baseline BL is determined based on the shape of the brightness profile of the part absorbed by the blood vessel. Thus, a brightness profile (distribution of density D relative to the position X) NP is obtained which is not dependent on the amount of incidence light. FIG. 14 shows the distribution of density D relative to position X, and the formation of the density profile NP as shown in the drawing. Next, the CPU 53a calculates the peak height h and half-width w based on the density profile NP. The obtained value h as a ratio of the light intensity absorbed by the measurement object blood vessel (blood) and the light intensity passing through the tissue area, and w is displayed as a length equivalent to the blood vessel diameter. Then, the CPU 53a calculates the uncorrected hemoglobin concentration D from equation (1) below, and stores the result in the frame memory 53e. (Step S105).

$$D = h/wn \tag{1}$$

Where n is a constant representing the non-linear shape spread of the scattered average width. When there is not light scattering, n=1, and when there is light scattering, n>1.

Next, the CPU 53a controls the light source I/O interface 53d, the same part as that imaged in step S101 is illuminated with a suitable amount of light by the light-emitting diodes R1 and R1 (step S106), and the image is captured by the imaging part 52 (step S107). Finally, the CPU 53a determines whether or not the average brightness of the region B exceeds 100 (step S108), and when the brightness does not exceed 100, the amount of current flowing to the light-emitting diodes R1 and R2 is adjusted using the light source I/O interface 53d to adjust the amount of light (step S109), and the process returns to step S107.

When the average brightness of the region B is over 100 (step S108:YES), the CPU 53a performs a process similar to that of step S104 on the image obtained in step S107 so as to obtain a density profile NP1 that is not dependent on the amount of incidence light and a brightness profile PF1 described layer (step S110). Next, the CPU 53a controls the light source I/O interface 53d, the same part as that imaged in step S101 is illuminated with a suitable amount of light by the light-emitting diodes L1 and L1 (step S111), and the image is captured by the imaging part 52 (step S112). Finally, the CPU 53a determines whether or not the average brightness of the region B exceeds 100 (step S113), and when the brightness does not exceed 100, the amount of current flowing to the light-emitting diodes L1 and L2 is increased using the light source I/O interface 53d to adjust the amount of light (step S114), and the process returns to step S112.

When the average brightness of the region B is over 100 (step S113:YES), the CPU 53a performs a process similar to that of step S104 on the image obtained in step S112 so as to obtain a density profile NP2 that is not dependent on the amount of incidence light and a brightness profile PF2 described layer (step S115).

Figure 15:
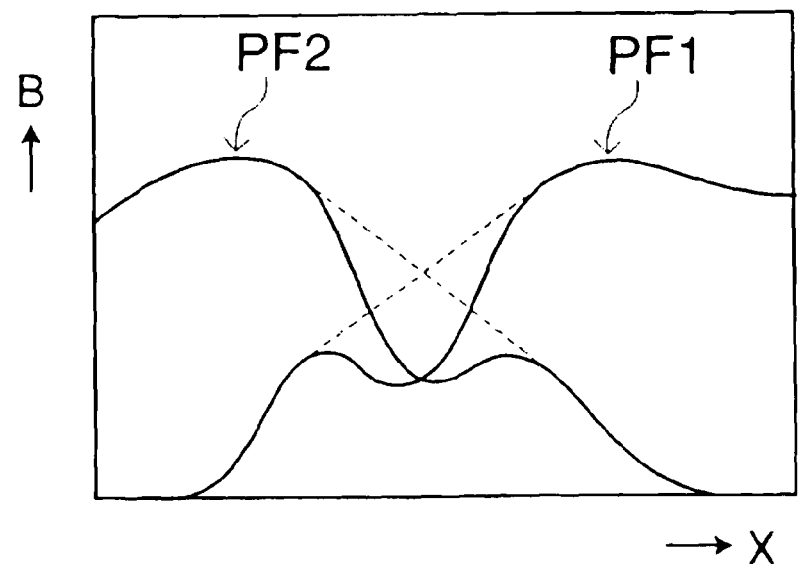
FIG. 15 shows a distribution of brightness B relative to position X.

FIG. 15 shows the distribution if the brightness B relative to the position X; as shown in the drawing, a brightness profile PF1 is formed n step S110, and a brightness profile PF2 is formed in step S115.

Figure 16:
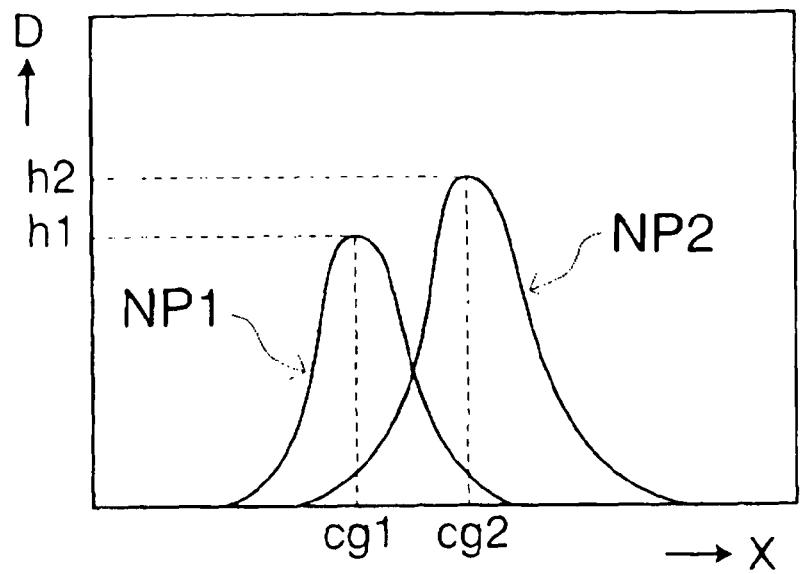
FIG. 16 shows a distribution of density D relative to position X.

FIG. 16 shows the distribution of the density D relative to the position X; as shown in the drawing, a density profile NP1 is formed in step S110, and a density profile NP2 is formed in step S115.

The CPU 53a calculates the peak height h and center coordinate cg1 from the density profile NP1 obtained in step S110, and calculates a peak height h and center coordinate cg2 from the density profile NP2 obtained in step S115, then calculates the blood vessel depth index S by the following equation (2) using these obtained data. Then, the CPU 53a stores the calculation results in the frame memory 53e (step S116).

$$S = (cg2 - cg1)/\{(h1+h2)/2\} \tag{2}$$

Next, the CPU 53a controls the light source I/O interface 53d, and the living body in the vicinity of the imaging region CR is illuminated with a suitable amount of light by the light-emitting diode SL1. The light reflected by the living body is received by the photosensor LTR, and the CPU 53a measures the amount of light v1 using the light source I/O interface 53d, and stores the calculation result in the frame memory 53e (step S117).

Next, the CPU 53a controls the light source I/O interface 53d, and the living body in the vicinity of the imaging region CR is illuminated with a suitable amount of light by the light-emitting diode SL2. The light reflected by the living body is received by the photosensor LTR, and the CPU 53a measures the amount of light v2 using the light source I/O interface 53d, and stores the calculation result in the frame memory 53e (step S118).

Next, the CPU 53a controls the light source I/O interface 53d, and the living body in the vicinity of the imaging region CR is illuminated with a suitable amount of light by the light-emitting diode SR1. The light reflected by the living body is received by the photosensor RTR, and the CPU 53a measures the amount of light v3 using the light source I/O interface 53d, and stores the calculation result in the frame memory 53e (step S119).

Next, the CPU 53a controls the light source I/O interface 53d, and the living body in the vicinity of the imaging region CR is illuminated with a suitable amount of light by the light-emitting diode SR2. The light reflected by the living body is received by the photosensor RTR, and the CPU 53a measures the amount of light v4 using the light source I/O interface 53d, and stores the calculation result in the frame memory 53e (step S120).

The tissue blood index M is calculated by equation (3) using the results obtained in steps S117, S118, S119, and S120 (step S121).

$$M = \{\log(v1/v2) + \log(v3+v4)\}/2 \tag{3}$$

The CPU 53a derives a correction value fm based on the tissue blood index M calculated in step S121, and a correction value fs based on the blood vessel depth S calculated in step S116, and using these results calculates a corrected hemoglobin concentration Do by equation (4) (step S122).

$$Do = D \times fs \times fm \tag{4}$$

The CPU 53a stores the calculation result of step S122 in the frame memory 53e (step S123), and the process returns to the main routine.

Figure 17:
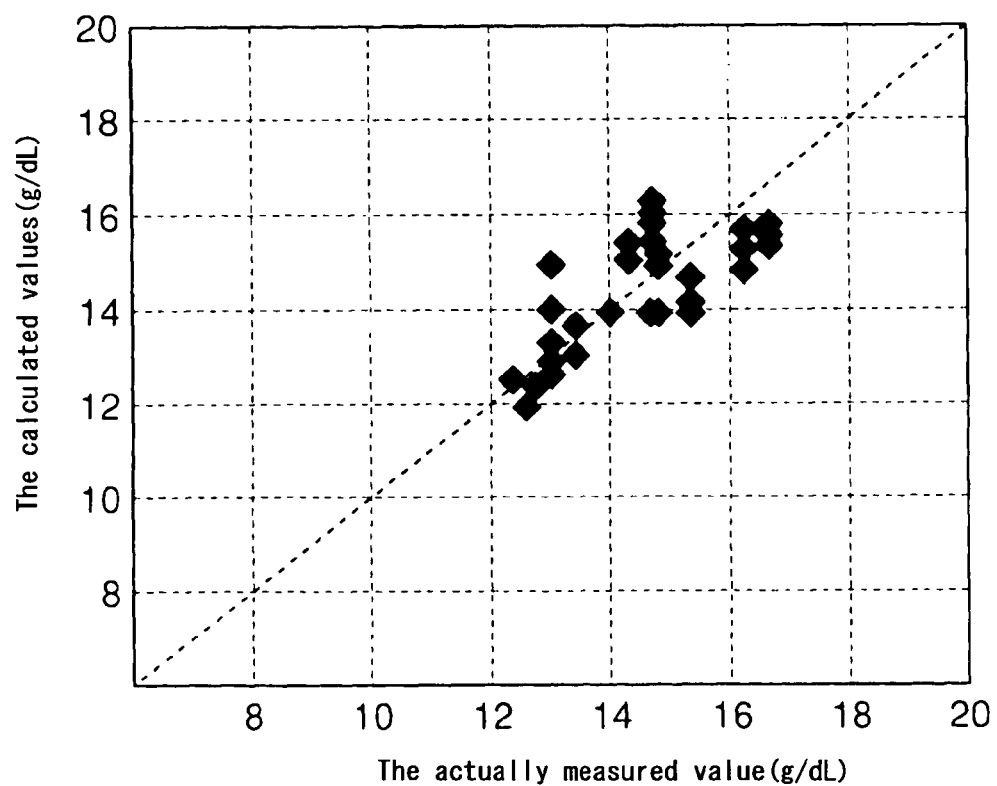
FIG. 17 is a graph plotting the calculation values of the non-invasive living body measuring device 1 of an embodiment of the present invention, and the actual measurement values obtained by a blood analyzer relative to the hemoglobin concentrations of several subjects.

FIG. 17 is a graph plotting the calculation values of the non-invasive living body measuring device 1 of an embodiment of the present invention, and the actual measurement values obtained by a blood analyzer relative to the hemoglobin concentrations of several subjects. As shown in FIG. 17, the actual measurement values and the calculated values of the non-invasive living body measuring device 1 are in the vicinity of a straight line of slope 1, and since there is no discrepancy between the actual measurement values and the calculated values, it can be understood that the non-invasive living body measuring device 1 is capable of measuring hemoglobin concentration with a high degree of accuracy.

Second Embodiment

Figure 18:
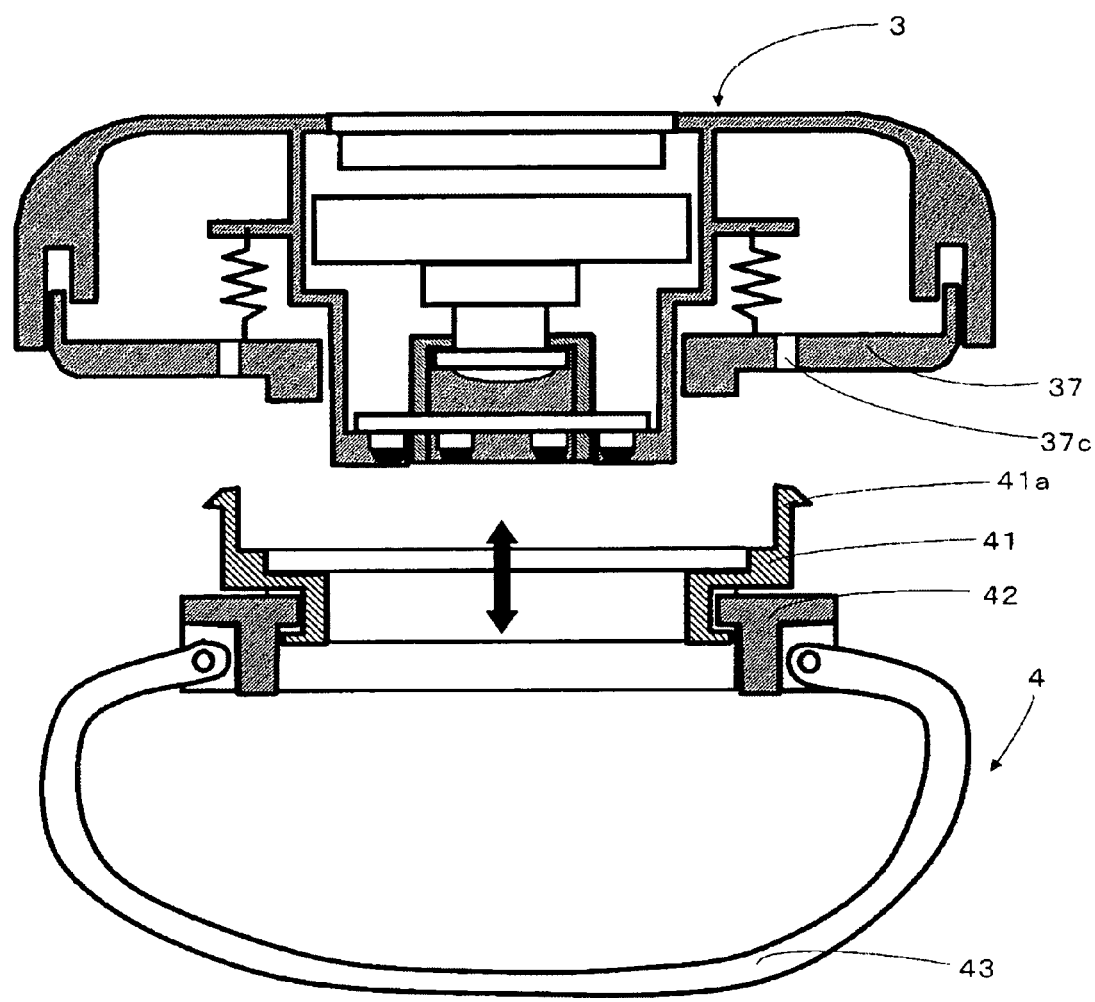
FIG. 18 is a cross section view showing the structure of a non-invasive living body measuring device 1 of a second embodiment of the present invention.

FIG. 18 is a cross section view showing the structure of a non-invasive living body measuring device 1 of a second embodiment of the present invention. The non-invasive living body measuring device 1 has a detachable connecting member 41 and back cover 37 described later mounted thereon, but in other respects has the same structure as the non-invasive living body measuring device 1 of the first embodiment; therefore, like structural elements are designated by like reference numbers and their further descriptions are omitted. As shown in FIG. 18, an opening 37*c* for engaging the connecting member 41 is provided in the back cover 37. A hook 41*a* for engaging the opening 37*c* projects from the connecting part 41. The back cover 37 and connecting member 41 are detachably mounted when the opening 37*c* and the hook 41*a* are engaged. According to this configuration, the user can remove the device body 3 from the connecting member 41.

Figure 19:
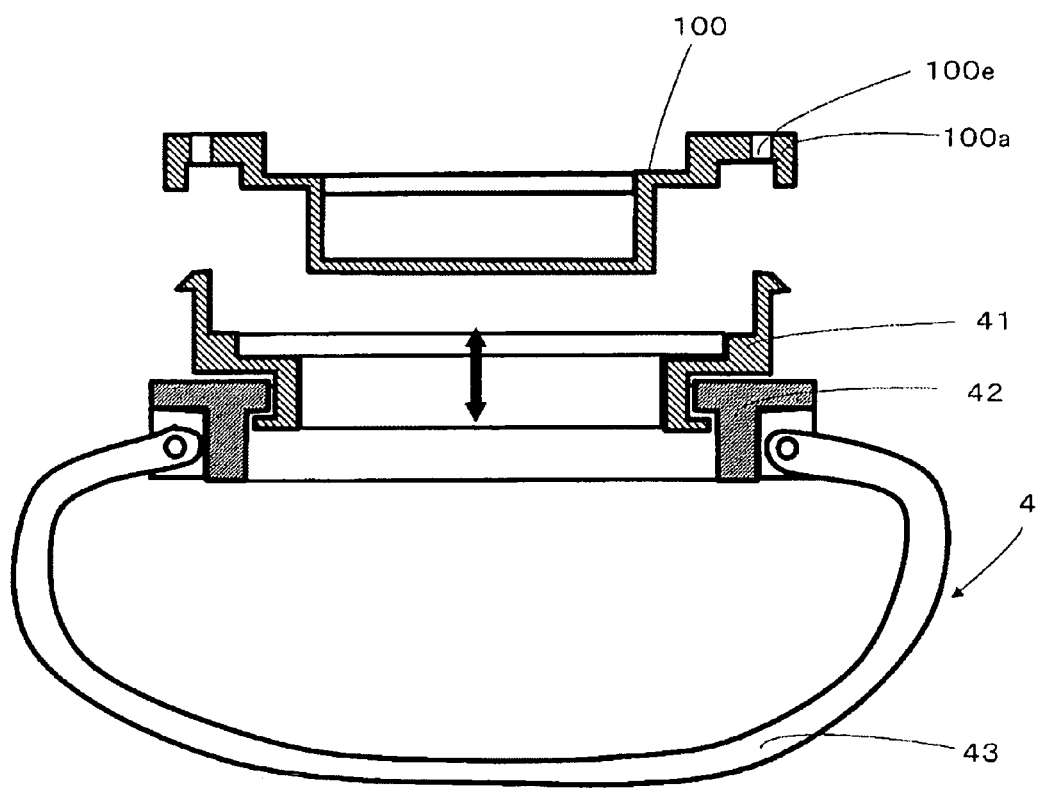
FIG. 19 is a cross section view of the holder 4 and the position adjustable cover 100.
Figure 20:
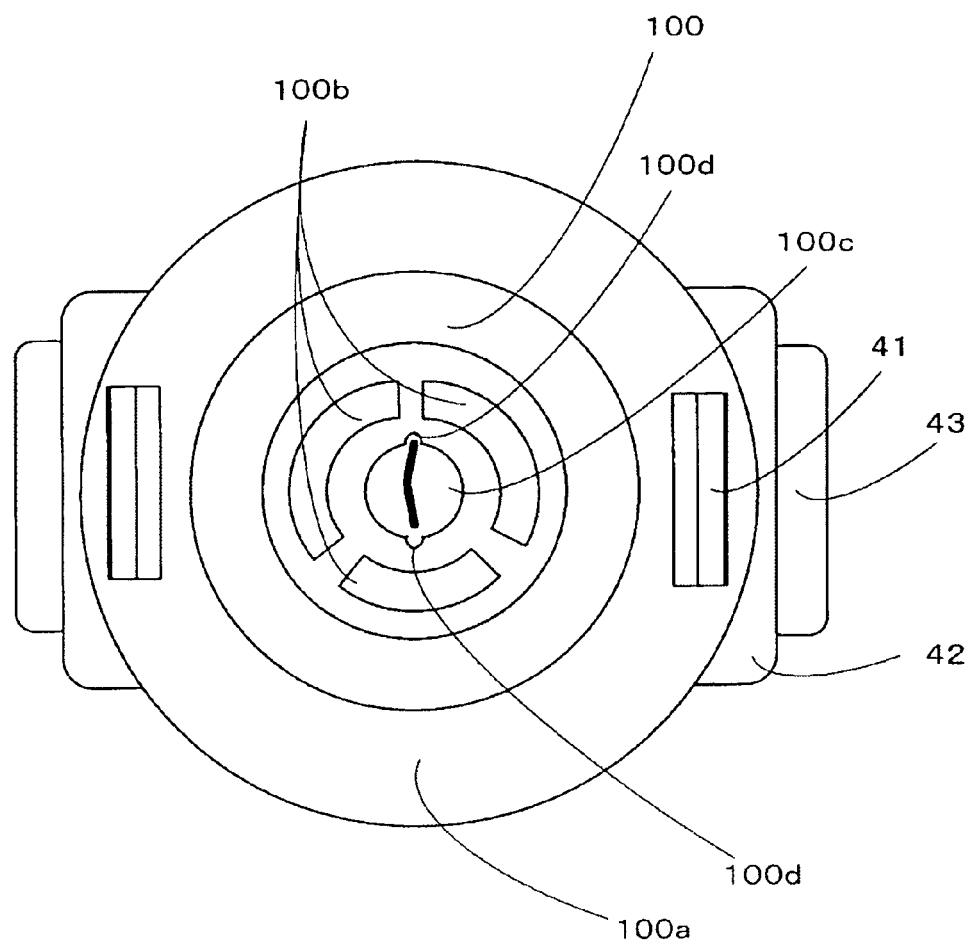
FIG. 20 is a top view of the position adjustable cover 100.

A position adjustment cover 100 is mounted on the connecting member 41 after the device body 3 has been removed, in order to adjust the position of the device body 3 at a position suited for imaging a blood vessel by the imaging part 52. FIG. 19 is a cross section view of a holder 4 and position adjustment cover 100, and FIG. 20 is a top view of the position adjustment cover 100. As shown in FIG. 19, the position adjustment cover 100 is cylindrical and can be inserted in the empty space of the connecting member 41. One end is opened, and provided with a flange 100*a* along the exterior perimeter of the open end. A connecting part configured by an opening 100*e* for engaging the connecting member 41 is provided on the flange 100*a* along a shape that matches the connecting part 41. The position adjustment cover 100 can be installed on the connecting member 41 by engaging the opening 100*e* and the hook 41*a*. Since the connecting member 41 is rotatable on the support platform 42 when engaged, the position adjustment cover 100 is rotatably supported by the support platform 42. As shown in FIG. 20, a plurality of slit holes 100*b* are formed in a ring shape in the bottom center of the position adjustment cover 100 and the outside margin of the slit holes is the same size as the hole diameter of the connecting member 41. An opening 100*c* is provided in the inside part of the slit holes 10*b*, and a pair of channels 100*d* are formed at the margin thereof. The pair of channels 100*d* include a region 62*c* between index lines 62*a* and 62*b* when the device body 3 is mounted. Thus, the user rotates the position adjustment cover 100 to adjust the position of the connecting member 41 and support platform 42 so as to be on a line of the depression of the two channels 100*d* and the measurement target the blood vessel while observing the engorged blood vessel in the wrist. After this position adjustment is completed, the device body 3 is again mounted on the connecting part 41, and the imaging part 52 is positionally adjusted to a suitable position for imaging the blood vessel.

The measurement operation performed by the non-invasive living body measuring device 1 is described below. The user installs the holder 4 with the position adjustment cover 100 mounted thereon on a wrist, and applies the pressure band 2 on the arm nearer the heart than the wrist. The user applies a predetermined pressure to the arm using the pressure band 2, and the blood vessels of the wrist become swollen. The user rotates the position adjustment cover 100 to so as to be on a line of the depression of the two channels 100*d* and the measurement target the blood vessel while observing the engorged blood vessel in the wrist to which pressure is applied. Thereafter, the position adjustment cover 100 is removed, and the device body 3 is mounted on the connecting member 41, as shown in FIG. 18. The subsequent measurement operation is identical to the description in the first embodiment and is therefore omitted.

Thus, since the imaging part 52 can be positionally adjusted to a position suited for imaging via observation, the imaging part 52 can be positionally adjusted by a slight movement compared to adjusting the position of the device body 3 by simply observing the index lines 62*a* and 62*b* and blood vessel pattern 61 in the image displayed on the display part 54, thus reducing the time for position adjustment.

Third Embodiment

The non-invasive living body measuring device 1 of a third embodiment is described below. The non-invasive living body measuring device 1 displays a blood vessel pattern 61 and index lines 62*a* and 62*b* on the display part 54 as shown in the first embodiment when positioning the blood vessel. Alternatively, the control part 53 may specify the position of a blood vessel, and determine whether or not the blood vessel is positioned within the region 62*c* between the index lines 62*a* and 62*b* stored in the flash memory card 53*j*. When the control part 53 determines that the blood vessel is not positioned within the region 62*c*, the screen of the display part 54 becomes red, and the direction markers 63, 64, 65, and 66 are lighted to indicate the direction in which to move the device body 3 as to position the blood vessel within the region 62*c* similar to the first embodiment. When the control part 53 determines that the blood vessel is within the region 62*c*, the screen of the display part 54 become blue, the power/execute key 38 become valid, and measurement starts when the user presses the key 38.

The subsequent process is identical to the description in the first embodiment and is therefore omitted.

In the non-invasive living body measuring device 1 of the first and second embodiments, the non-invasive living body measuring device is provided to warn whether or not a blood vessel is positioned within a region suited for imaging by the imaging part 52, the user is alerted to this suitability by changing the display color of the index lines 62*a* and 62*b*. In the non-invasive living body measuring device 1 of the third embodiment, however, the user is alerted to the suitability by changing the display color of the screen of the display part 54. However, the alerting means is not limited to this arrangement inasmuch as, for example, the user may be alerted by sound when the a blood vessel is positioned within a region suited for imaging by the imaging part 52, or an LED can be provided such that the user is alerted by whether or not the LED is lighted.

Although the non-invasive living body measuring device 1 of the first and second embodiments are described in terms of displaying both a captured image and blood vessel pattern 61 and index lines 62*a* and 62*b* on the display part 54, the present invention is not limited to this arrangement inasmuch as the blood vessel pattern 61 and index lines 62*a* and 62*b* can be displayed on the display part 54 without displaying the captured image.

Although the non-invasive living body measuring device 1 of the second embodiment has been described in terms of a position adjustment cover 100 mountable on a connecting member 41 after the device body 3 has been removed, the present invention is not limited to this arrangement inasmuch as a position adjustment member and connecting member 41 may be integratedly formed to position the device body 3 at a position suited for imaging a blood vessel by the imaging part 52.

Figure 21:
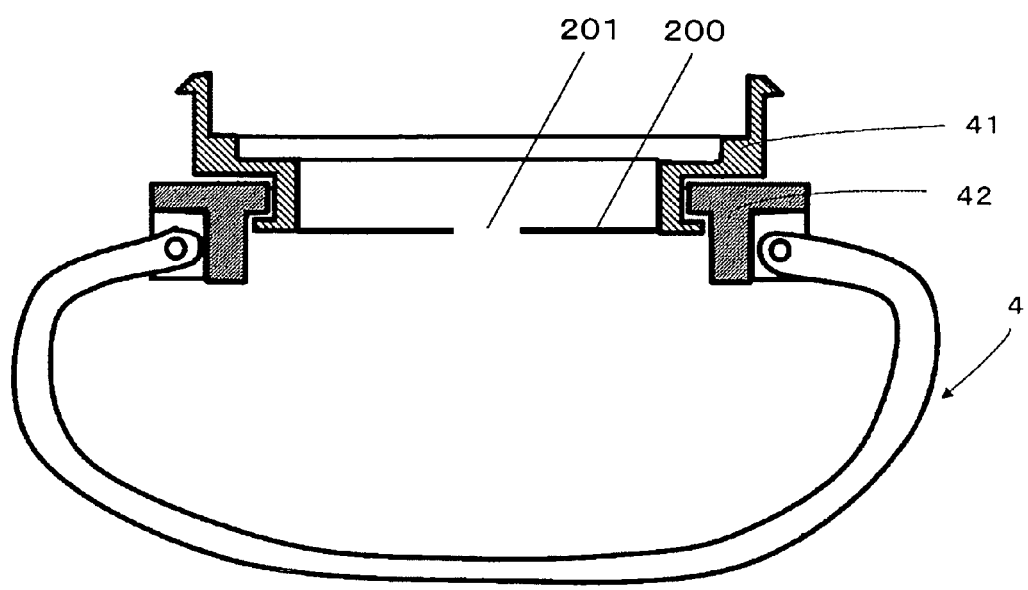
FIG. 21 is a cross section view of the holder 4.

Modifications of the second embodiment are described below using FIGS. 21 and 22. FIG. 21 shows a cross section view of a holder 4 with the device body 3 of the non-invasive living body measuring device 1 removed. The holder 4 is configured by a connecting member 41 for mounting a device body, and a support platform 42 for rotatably supporting the connecting member 41. The bottom surface of the connecting member 41 is provided with a position adjustment member 200 for adjusting the position of a device body 3 to a position suited for imaging a blood vessel by the imaging part 52. An opening 201 is provided in the position adjustment member 200.

Figure 22:
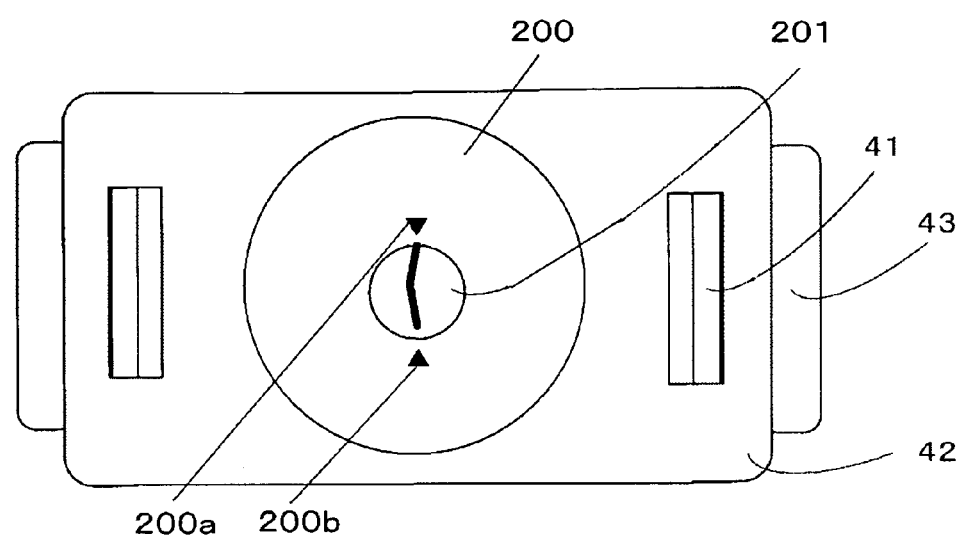
FIG. 22 is a top view of the holder 4.

FIG. 22 is a top view of the holder 4. Markers 200a and 200b are provided on the position adjustment member 200 for placing a blood vessel at a position suited for imaging. The user observes the engorged blood vessel through the opening 201, and rotates the connecting member 41 provided with the position adjustment member 200 relative to the support platform 42 so as to place the markers 200a and 200b and the measurement target blood vessel on a line. After the adjustment, the device body 3 is mounted on the holder 4, and measurement is performed. Although an opening 201 is provided in the position adjustment member 200, the opening 201 need not be provided if the position adjustment member 200 is formed of transparent material, such that the user can place the markers 200a and 200b and the measurement target blood vessel on a line while observing the engorged blood vessel in the wrist through the transparent material.

Furthermore, although the non-invasive living body measuring device 1 on the first embodiment has been described in terms of displaying index lines 62a and 62b on the display part 54, the present invention is not limited to this arrangement inasmuch as the index lines 62a and 62b may be adhered to the screen of the display part 54 so as to provide the index lines 62a and 62b on the display part 54.

What is claimed is:

1. A non-invasive living body measuring device for measuring components contained in a blood, comprising:
    a device body; and
    a mounting part that is configured to be movably mountable on a wrist of a living body and holds the device body,
    wherein the device body comprises:
        an imaging part including a lens and an image pickup element, and configured to image the wrist of the living body by the image pickup element through the lens;
        a display part; and
        a controller that displays an image of the wrist obtained by the imaging part on the display part, generates a blood vessel image showing a blood vessel within the obtained image of the wrist, and displays the generated blood vessel image and two index lines on the display part, a region between the two index lines representing a suitable region for imaging a blood vessel by the imaging part,
    wherein the mounting part holds the device body so as to be rotatable around an optical axis of the lens, and
    wherein the controller measures the components in a blood by analyzing a blood vessel image of the wrist obtained by the imaging part.

2. The non-invasive living body measuring device according to claim 1, wherein
    the blood vessel image is a blood vessel pattern generated based on a pixel of a lowest brightness in brightness distribution determined in a fixed direction from a plurality of specific pixels in the image of the wrist.

3. The non-invasive living body measuring device according to claim 1, wherein
    the controller determines whether or not the blood vessel image is positioned within the two index lines.

4. The non-invasive living body measuring device according to claim 3, further comprising
    an execution key for starting a measurement,
    wherein the execution key is valid when the controller determines that the blood vessel image is positioned within the two index lines.

5. The non-invasive living body measuring device according to claim 3, further comprising:
    an alerting part;
    wherein when the controller determines that the blood vessel image is positioned within the two index lines, the alerting part alerts the user that the blood vessel is positioned within the region suitable for image the blood vessel.

6. The non-invasive living body measuring device according to claim 3, further comprising:
    an alerting part;
    wherein when the controller determines that the blood vessel image is not positioned within the two index lines, the alerting part alerts the user to a direction in which to move the device to bring the blood vessel within the two index lines.

7. The non-invasive living body measuring device according to claim 3, wherein:
    the controller changes a color of the two index lines when the controller determines that the blood vessel image is positioned within the two index lines.

8. The non-invasive living body measuring device according to claim 1, wherein when the blood vessel image is not positioned within the two index lines, the controller displays on the display part a direction in which to move the device body so as to bring the blood vessel image within the two index lines.

9. The non-invasive living body measuring device according to claim 1, wherein the controller displays the two index lines at a predetermined position on the display part.

10. A non-invasive living body measuring device for measuring components contained in a blood, comprising:
    a device body; and
    a mounting part that is configured to be movably mountable on a wrist of a living body and holds the device body,
    wherein the device body comprises:
        an imaging part including a lens and an image pickup element, and configured to image the wrist of the living body by the image pickup element through the lens;
        a display part;
        a controller that displays an image of the wrist obtained by the imaging part on the display part, generated a blood vessel image showing a blood vessel within the obtained image of the wrist, and displays the generated blood vessel image on the display part;
    wherein the display part is configured to display two index lines, a region between the two index lines representing a region suitable for imaging the blood vessel by the imaging part,
    wherein the mounting part holds the device body so as to be rotatable around an optical axis of the lens,
    and wherein the controller measures the components in a blood by analyzing a blood vessel image in the image of the wrist obtained by the imaging part.

* * * * *

UNITED STATES PATENT AND TRADEMARK OFFICE
CERTIFICATE OF CORRECTION

| | |
|---|---|
| PATENT NO. | : 7,962,189 B2 |
| APPLICATION NO. | : 11/485564 |
| DATED | : June 14, 2011 |
| INVENTOR(S) | : Shigehiro Numada et al. |

It is certified that error appears in the above-identified patent and that said Letters Patent is hereby corrected as shown below:

In the Claims

In column 14, claim 5, line 13, after "the region suitable for" replace "image" with --imaging--.

Signed and Sealed this
Twenty-fifth Day of October, 2011

David J. Kappos
*Director of the United States Patent and Trademark Office*